US008268832B2

(12) United States Patent
Wilkinson et al.

(10) Patent No.: US 8,268,832 B2
(45) Date of Patent: *Sep. 18, 2012

(54) MALEATE SALTS OF 6-(5-CHLORO-2-PYRIDYL)-5-[(4-METHYL-1-PIPERAZINYL)CARBONYLOXY]-7-OXO-6,7-DIHYDRO-5H-PYRROLO[3,4-B]PYRAZINE

(75) Inventors: H. Scott Wilkinson, Westborough, MA (US); Richard Hsia, Southborough, MA (US); Tushar Misra, Leesburg, VA (US); Kostas Saranteas, Peabody, MA (US); Patrick Mousaw, Granger, IN (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/338,908

(22) Filed: Dec. 18, 2008

(65) Prior Publication Data

US 2009/0215784 A1    Aug. 27, 2009

Related U.S. Application Data

(60) Provisional application No. 61/008,364, filed on Dec. 19, 2007.

(51) Int. Cl.
*A61K 31/4965* (2006.01)
(52) U.S. Cl. .................................. 514/255.01
(58) Field of Classification Search ............. 514/255.01
See application file for complete search history.

(56) References Cited

U.S. PATENT DOCUMENTS

| | | | |
|---|---|---|---|
| 3,862,149 A | 1/1975 | Cotrel et al. |
| 5,786,357 A | 7/1998 | Young et al. |
| 6,319,926 B1 | 11/2001 | Cotrel et al. |
| 6,436,936 B1 | 8/2002 | Young et al. |
| 6,444,673 B1 | 9/2002 | Cotrel et al. |
| 6,864,257 B2 | 3/2005 | Cotrel et al. |
| 7,125,874 B2 | 10/2006 | Cotrel et al. |
| 7,381,724 B2 | 6/2008 | Cotrel et al. |
| 7,465,729 B2 | 12/2008 | Wessel et al. |
| 7,776,858 B2 | 8/2010 | Wessel et al. |
| 2005/0164987 A1 | 7/2005 | Barberich |
| 2005/0176680 A1 | 8/2005 | Lalji et al. |
| 2005/0215521 A1 | 9/2005 | Lalji et al. |
| 2005/0222156 A1 | 10/2005 | Wessel et al. |
| 2005/0267176 A1 | 12/2005 | Barberich |
| 2006/0051412 A1 | 3/2006 | Petereit et al. |
| 2007/0098788 A1 | 5/2007 | Gore et al. |
| 2007/0270590 A1 | 11/2007 | Mendelovici et al. |
| 2007/0299055 A1 | 12/2007 | Lalji et al. |
| 2008/0027223 A1 | 1/2008 | Mainfeld et al. |
| 2008/0175903 A1 | 7/2008 | Hopkins et al. |
| 2008/0293726 A1 | 11/2008 | Caron et al. |
| 2009/0111817 A1 | 4/2009 | Caron et al. |
| 2009/0111818 A1 | 4/2009 | Caron et al. |
| 2009/0209545 A1 | 8/2009 | Hsia et al. |
| 2009/0209546 A1 | 8/2009 | Wilkinson et al. |
| 2010/0004251 A1 | 1/2010 | Barberich |
| 2010/0009994 A1 | 1/2010 | Wilkinson et al. |
| 2010/0009995 A1 | 1/2010 | Wilkinson et al. |
| 2010/0221338 A1 | 9/2010 | Hsia et al. |
| 2010/0280038 A1 | 11/2010 | Wessel et al. |
| 2011/0009416 A1 | 1/2011 | Hsia et al. |
| 2011/0053945 A1 | 3/2011 | Wilkinson et al. |

FOREIGN PATENT DOCUMENTS

| | | |
|---|---|---|
| CN | 1418631 | 5/2003 |
| CN | 1854137 | 11/2006 |
| EP | 1005863 | 7/2000 |
| EP | 1166801 | 2/2002 |
| WO | 9310787 A | 6/1993 |
| WO | 2005060968 A | 7/2005 |
| WO | 2005063248 A | 7/2005 |
| WO | WO2005063297 | 7/2005 |
| WO | WO2005079851 | 9/2005 |
| WO | 2005097132 A | 10/2005 |
| WO | WO 2006/002836 | 1/2006 |
| WO | 2007006003 A | 1/2007 |
| WO | WO2007005961 | 1/2007 |
| WO | WO2007005962 | 1/2007 |
| WO | WO2007005940 | 6/2007 |
| WO | IN2007083188 A | 7/2007 |
| WO | WO 2008/002629 | 1/2008 |
| WO | WO2008070000 | 6/2008 |
| WO | WO 2009/085988 | 7/2009 |

(Continued)

OTHER PUBLICATIONS

Spealman, R. D. J. Pharmacol. Exp. Ther., 235(2), 1985, 456-462.*
Berge, et al. J. Pharm. Sci., 66(1), 1977, 1-19.*
International Search Report and Written Opinion for corresponding International Patent Application No. PCT/US2008/087489 dated Mar. 18, 2009.
International Search Report and Written Opinion for corresponding International Patent Application No. PCT/US2008/087461 dated Mar. 19, 2009.
Machine translation of CN 1854137 (Nov. 2006) Wang et al.

*Primary Examiner* — Douglas M Willis
(74) *Attorney, Agent, or Firm* — Heslin Rothenberg Farley & Mesiti P.C.

(57) ABSTRACT

Pharmaceutical compositions of maleate salts of (6-(5-chloro-2-pyridyl)-5-[(4-methyl-1-piperazinyl)carbonyloxy]-7-oxo-6,7-dihydro-5H-pyrrolo [3,4-b]pyrazine) are provided. The maleate salts are sleep agents useful in oral dosage forms.

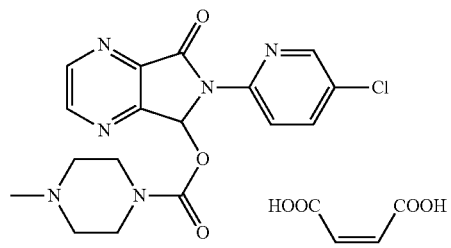

2 Claims, 1 Drawing Sheet

FOREIGN PATENT DOCUMENTS

| | | |
|---|---|---|
| WO | WO2009085972 | 7/2009 |
| WO | WO 2010/088385 | 8/2010 |
| WO | WO2010088385 | 8/2010 |
| WO | WO2011005250 | 1/2011 |

* cited by examiner

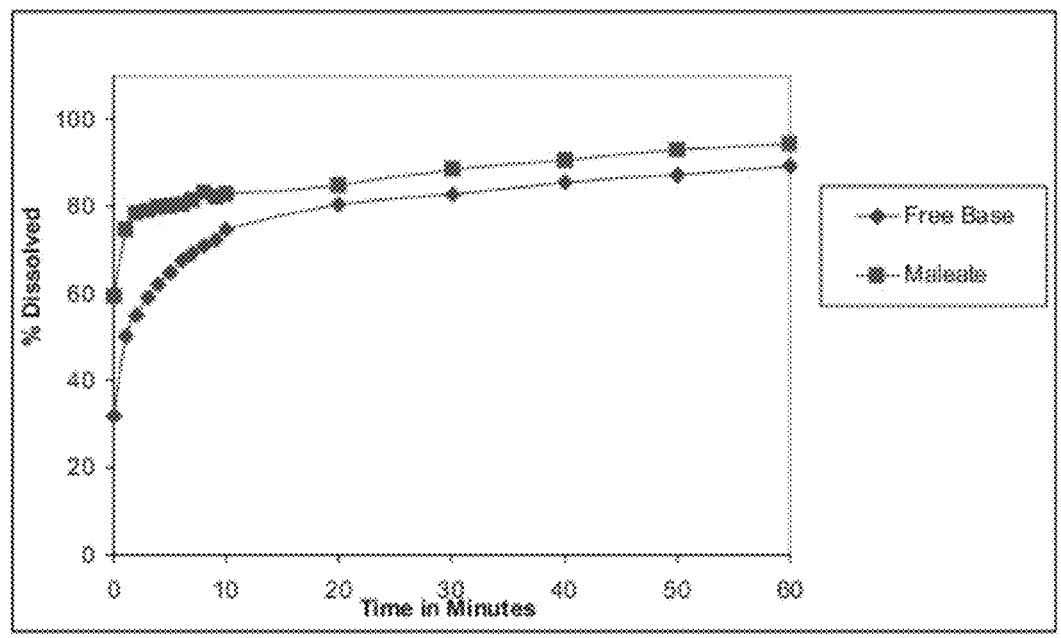

MALEATE SALTS OF 6-(5-CHLORO-2-PYRIDYL)-5-[(4-METHYL-1-PIPERAZINYL)CARBONYLOXY]-7-OXO-6,7-DIHYDRO-5H-PYRROLO[3,4-B]PYRAZINE

RELATED APPLICATIONS

This application claims priority to U.S. Provisional Application No. 61/008,364, filed Dec. 19, 2007, which is incorporated by reference herein in its entirety.

FIELD OF THE INVENTION

The present invention provides a novel maleate salt of (6-(5-chloro-2-pyridyl)-5-[(4-methyl-1-piperazinyl)carbonyloxy]-7-oxo-6,7-dihydro-5H-pyrrolo[3,4-b]pyrazine), which exhibits superior taste characteristics and improved aqueous solubility/dissolution behavior compared to the free base. The maleate salt is thus useful for pharmaceutical dosage forms, particularly for oral dosage forms.

BACKGROUND OF THE INVENTION

Eszopiclone, also known as (S)-zopiclone or (S)-(6-(5-chloro-2-pyridyl)-5-[(4-methyl-1-piperazinyl)carbonyloxy]-7-oxo-6,7-dihydro-5H-pyrrolo[3,4-b]pyrazine), is formulated as the free base and is sold as LUNESTA®. It is used to treat different types of sleep problems, such as difficulty in falling asleep, difficulty in maintaining sleep during the night, and waking up too early in the morning. Most people with insomnia have more than one of these problems. See, e.g., WO 93/10787; Brun, J. P., *Pharm. Biochem. Behav.* 29: 831 832 (1988).

The compound eszopiclone and various methods of treatment are disclosed at least in the following U.S. Pat. Nos. 7,125,874; 6,864,257; 6,444,673; 6,319,926; and 5,786,357.

Racemic zopiclone, rac-(6-(5-chloro-2-pyridyl)-5-[(4-methyl-1-piperazinyl)carbonyloxy]-7-oxo-6,7-dihydro-5H-pyrrolo[3,4-b]pyrazine), also formulated as the free base, has been sold in Europe for many years to treat different types of sleep problems.

SUMMARY OF THE INVENTION

In one aspect, the present invention provides a composition comprising the maleate salt of racemic or enantioenriched zopiclone: (6-(5-chloro-2-pyridyl)-5-[(4-methyl-1-piperazinyl)carbonyloxy]-7-oxo-6,7-dihydro-5H-pyrrolo[3,4-b]pyrazine), having the formula

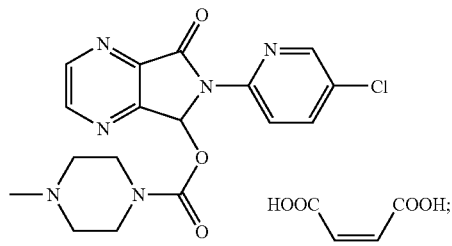

as well as pharmaceutical dosage forms thereof.

In another aspect, the present invention provides a composition comprising the maleate salt of eszopiclone: (6-(5-chloro-2-pyridyl)-5-[(4-methyl-1-piperazinyl)carbonyloxy]-7-oxo-6,7-dihydro-5H-pyrrolo[3,4-b]pyrazine), having the formula

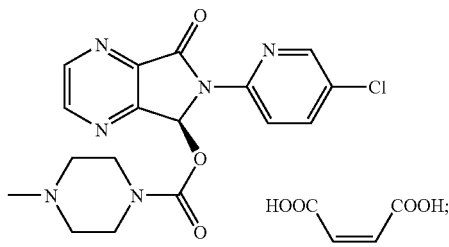

as well as pharmaceutical dosage forms thereof.

It has been found that this maleate salt can exhibit superior taste characteristics as well as improved aqueous solubility/dissolution behavior compared to the free base.

The invention is also directed towards a method for treating a sleep disorder in a subject comprising administering to a subject in need thereof the maleate salt of zopiclone or eszopiclone.

In another aspect, the invention provides a method for treating anxiety in a subject comprising administering to a subject in need thereof the maleate salt of zopiclone or eszopiclone.

In one aspect, the invention provides a composition described above wherein the composition has at least a one unit difference on an E-tongue analysis relative to eszopiclone.

In another aspect, the invention is directed towards a composition formed by reacting 6-(5-chloro-2-pyridyl)-5-[(4-methyl-1-piperazinyl)carbonyloxy]-7-oxo-6,7-dihydro-5H-pyrrolo[3,4-b]pyrazine and maleic acid.

In another aspect, the invention provides a method of making a maleate salt of 6-(5-chloro-2-pyridyl)-5-[4-methyl-1-piperazinyl)carbonyloxy]-7-oxy-6,7-dihydro-5H-pyrrolo[3,4-b]pyrazine, comprising the steps of: admixing zopiclone or eszopiclone in one or more solvents, admixing maleic acid with the zopiclone or eszopiclone, and isolating the maleate salt.

In another aspect, the invention provides a method of making a maleate salt of 6-(5-chloro-2-pyridyl)-5-[4-methyl-1-piperazinyl)carbonyloxy]-7-oxy-6,7-dihydro-5H-pyrrolo[3,4-b]pyrazine, comprising the steps of: a) dissolving zopiclone or eszopiclone in an organic solvent; b) heating to form a composition; c) dissolving maleic acid in a solvent to form a composition; d) transferring the composition of step c) to the solution of step b), or transferring the composition of step b) to the solution of step c), or admixing the composition of step b) and step c); e) cooling to form a salt; and f) isolating the maleate salt. In certain instances, the composition of step e) is filtered and washed with one or more solvents. In certain instances, the salt is isolated and in certain instances the salt is dried.

BRIEF DESCRIPTION OF THE DRAWINGS

FIG. 1 depicts an exemplary dissolution profile of the maleate salt compared to free base eszopiclone.

DETAILED DESCRIPTION

Salts of the Invention

In one aspect, the present invention provides a composition having the formula

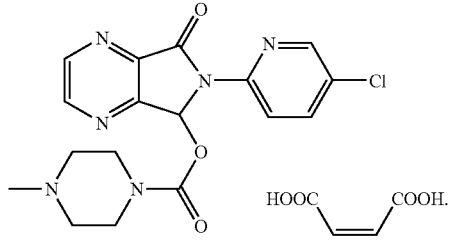

(1)

In another aspect, the invention provides a composition having the formula

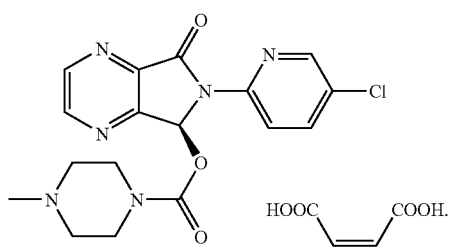

(2)

In another aspect, the invention provides a pharmaceutical dosage form comprising the maleate salt of zopiclone or eszopiclone and a pharmaceutically acceptable carrier.

In another aspect, the invention provides a composition formed by reacting 6-(5-chloro-2-pyridyl)-5-[(4-methyl-1-piperazinyl)carbonyloxy]-7-oxo-6,7-dihydro-5H-pyrrolo[3,4-b]pyrazine and maleic acid.

As used herein, the terms zopiclone and 6-(5-chloro-2-pyridyl)-5-[(4-methyl-1-piperazinyl)carbonyloxy]-7-oxo-6,7-dihydro-5H-pyrrolo[3,4-b]pyrazine refer to compounds represented by the following structure:

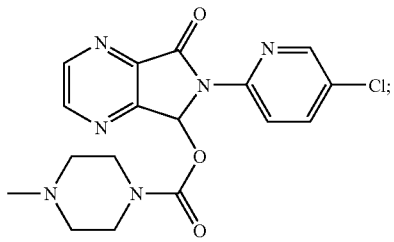

the terms eszopiclone, LUNESTA®, and [(9S)-8-(5-chloro-pyridin-2-yl)-7-oxo-2,5,8-triazabicyclo[4.3.0]nona-1,3,5-trien-9-yl]4-methyl piperazine-1-carboxylate refer to an individual enantiomer of the foregoing represented by the following structure:

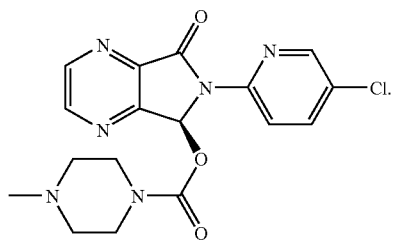

The maleate salt of the invention contemplates both the racemic mixture (also known as zopiclone), and in certain embodiments, contemplates a single enantiomer, e.g., the S-enantiomer (eszopiclone). Eszopiclone is the S-(+)-optical isomer of the compound zopiclone, which is described in U.S. Pat. Nos. 6,319,926 and 6,444,673, and in Goa and Heel (Drugs, 32:48-65 (1986)) and in U.S. Pat. Nos. 3,862,149 and 4,220,646. This isomer, which will hereinafter be referred to by its USAN-approved generic name, eszopiclone, includes the optically pure and the substantially optically pure (e.g., 90%, 95% or 99% optical purity) S-(+)-zopiclone isomer. As such, the maleate salt of this invention can exist as an individual stereoisomer as well as a mixture of stereoisomers. Accordingly, the maleate salt of the present invention will include not only a stereoisomeric mixture, but also individual respective stereoisomers substantially free from other stereoisomers. In certain embodiments, the maleate salt of the invention is directed towards stereochemically pure isomers or racemic mixtures. For example, it encompasses non-racemic mixtures of stereoisomers of the same compound (e.g., about 90, 80, 70, or 60 weight percent of one enantiomer and about 10, 20, 30, or 40 weight percent of the opposite enantiomer); and mixtures of different racemic or stereomerically pure compounds (e.g., about 90, 80, 70, or 60 weight percent of one compound and about 10, 20, 30, or 40 weight percent of another).

The compounds of the invention can be synthesized by techniques known in the art. The starting materials and certain intermediates used in the synthesis of the compounds of this invention are available from commercial sources or can themselves be synthesized using reagents and techniques known in the art, including those synthesis schemes delineated herein.

Racemic zopiclone is commercially available and can be made using various methods, such as those disclosed in U.S. Pat. Nos. 3,862,149 and 4,220,646.

The synthesis of the maleate salt of the invention can be carried out according to the reaction sequence of Scheme 1, and begins with dissolving (S)-zopiclone into an organic solvent. Organic solvents include, but are not limited to tetrahydrofuran, diethyl ether, methyl-t-butyl ether, toluene, cumene, chloroform, methylene chloride, hexanes, pentane, heptane, acetone, ethyl acetate, methanol, ethanol, propanol, i-PrOH, and butanol. The contents can be heated to dissolve. The reaction temperature can range from about 25° C. to about 100° C.; in certain embodiments the temperature can range from about 25° C. to about 50° C.; in certain embodiments the temperature can range from about 50° C. to about 100° C.

Maleic acid is dissolved into a solvent and is transferred slowly to the zopiclone solution at a temperature ranging from about 25° C. to about 100° C. The reaction is optionally seeded with maleate salt and allowed to cool with stirring and aged. Filtration and washing with a solvent or mixture of solvents is carried out followed by filtration. Mixtures of solvents used for washing and/or filtration include but are not limited to ratios of 1:1, 2:1, 3:1, 4:1, 5:1, 10:1, and 20:1. In certain embodiments, mixtures of three organic solvents can be used. The resulting salt is isolated and dried (optionally under vacuum) at a temperature ranging from about 25° C. to about 100° C., preferably about 60° C. to about 65° C., and packaged in an appropriate container.

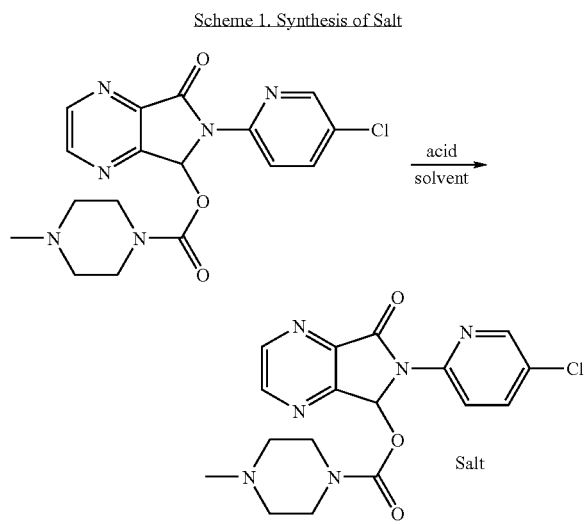

Higher order salts can also be prepared, e.g., salts having about 1:2 acid:eszopiclone. Such higher order salts can be prepared by using an appropriate molar excess of eszopiclone, which is easily determined by one of ordinary skill in the art. For example, two molar equivalents of eszopiclone to free acid form a 1:2 acid:eszopiclone composition.

The compounds of the present invention contain asymmetric carbon atoms. As such, a compound of this invention can exist as an individual stereoisomer as well as a mixture of stereoisomers. Accordingly, a compound of the present invention will include not only a stereoisomeric mixture, but also individual respective stereoisomers substantially free from other stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing stereoisomers are well known in the art and can be applied as practicable to final compounds or to starting material or intermediates. In another embodiment, the compound is an isolated compound.

Methods for optimizing reaction conditions, if necessary to minimize competing by-products, are known in the art. Additional reaction schemes and protocols can be determined by the skilled artesian by use of commercially available structure-searchable database software, for instance, SciFinder® (CAS division of the American Chemical Society) and Cross-Fire Beilstein® (Elsevier MDL), or by appropriate keyword searching using an internet search engine such as Google® or keyword databases such as the US Patent and Trademark Office text database.

The synthetic methods described herein can also additionally include steps, either before or after the steps described specifically herein, to add or remove suitable protecting groups in order to ultimately allow synthesis of the compound of the formulae described herein.

Methods of Treatment

In certain aspects, the invention provides a method for treating or preventing various disorders using a zopiclone maleate salt. In one embodiment, the invention provides a method for treating and/or preventing sleep disorders, including primary insomnia and sleep-awake rhythm disorders (e.g., work-shift syndrome, time-zone syndrome (jet-lag)).

Insomnia is characterized by difficulty in sleeping or disturbed sleep patterns. Insomnia can be of a primary nature with little apparent relationship to immediate somatic or psychic events, or secondary to some acquired pain, anxiety or depression.

In one aspect, the invention provides a method for treating or preventing a sleep disorder in a subject comprising administering to a subject in need thereof a salt composition having the formula

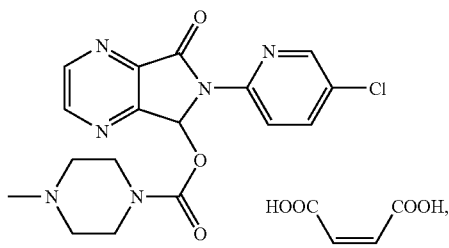

such that administration of the salt treats the sleep disorder.

In another aspect, the invention provides a method for treating or preventing anxiety in a subject comprising administering to a subject in need thereof a salt composition having the formula

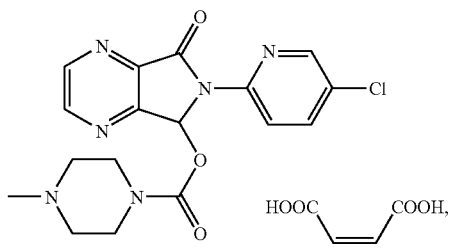

such that administration of the salt treats the anxiety.

As used herein the term "anxiety" refers to an anxiety disorder. Examples of anxiety disorders treatable by the compositions and methods disclosed herein include, but are not limited to: panic attack, agoraphobia, acute stress disorder, specific phobia, panic disorder, psychoactive substance anxiety disorder, organic anxiety disorder, obsessive-compulsive anxiety disorder, posttraumatic stress disorder and generalized anxiety disorder. Anxiety as referred to herein also includes situational anxiety (e.g. as experienced by a performer prior to a performance).

The named anxiety disorders have been characterized in the DSM-IV-R. Diagnostic and Statistical Manual of Mental Disorders, Revised, 4th Ed. (1994). The DSM-IV-R was prepared by the Task Force on Nomenclature and Statistics of the American Psychiatric Association, and provides clear descriptions of diagnostic categories.

In a further aspect, the invention provides a use of the maleate salt of zopiclone, particularly eszopiclone, for the treatment or prevention of a disorder disclosed herein. In a preferred embodiment, the disorder is sleep disorders or anxiety.

In a yet further aspect, the invention provides a use of the maleate salt of zopiclone, particularly eszopiclone, for the preparation of medicament for the treatment or prevention of a disorder disclosed herein. In a preferred embodiment, the disorder is sleep disorders or anxiety.

Preferred methods and uses of the invention include identifying and/or selecting a subject, particularly a human subject, that is susceptible to or suffering from a disorder disclosed herein, and thereafter administering to the identified and selected subject the maleate salt of zopiclone, particularly eszopiclone. In certain embodiments, the disorder is sleep disorders or anxiety. Such identification and selection can be made e.g., by a physician or other health professional.

Other disorders treated by the invention include seasonal melancholia, genital disorder, neuroendocrine disorder, senile dementia, Alzheimer's disease, various disorders accompanied by aging, cerebrovascular disorders (e.g. cerebral hemorrhage, etc.), cranial injury, spinal injury, epilepsy, depression, manic-depressive psychosis, schizophrenia, alcoholism, Parkinson's disease, hypertension, arteriosclerosis, arrhythmia, premenstrual tension syndrome, glaucoma, metabolic disorders (e.g., obesity, insulin resistance, etc.), cancer, AIDS and diabetes in mammals (e.g. human, cat, dog, monkey, etc.). In addition, it is also effective for protection against aging, immunoregulation, and ovulatory regulation (e.g., contraception).

In one embodiment, the invention provides a method of treating or preventing a disease or condition which is affected by the modulation of one or more central benzodiazepine sites in a subject which comprises administering to a subject in need of such treatment or prevention a therapeutically or prophylactically effective amount of a zopiclone maleate salt. Such disorder include but are not limited to anxiety; affective disorders such as depression, attention deficit disorder ("ADD"), and attention deficit disorder with hyperactivity ("ADDH") or attention deficit/hyperactivity disorder ("ADHD"); convulsive disorders such as epilepsy; aggressive behavior; spasticity or acute muscle spasm; behavioral disorders such as mood anxiety and schizophrenia; and alcohol and drug addiction.

Another embodiment of the invention encompasses a method of treating or preventing anxiety in a subject which comprises administering to a subject in need of such treatment or prevention a therapeutically or prophylactically effective amount of a zopiclone maleate salt. The anxiety can be acute or chronic anxiety, or can be a general anxiety disorder. In certain embodiments, the invention provides for reducing the severity of at least one symptom associated with acute anxiety, chronic anxiety, general anxiety disorder caused by psychologic and/or physiologic factors, and other anxiety disorders such as panic disorders, mood anxiety, panic attacks, phobias, obsessive-compulsive disorders, or post traumatic distress disorder. Symptoms associated with acute anxiety include, but are not limited to, a fear of losing control of one's own actions, a sense of terror arising from no apparent reason, and a dread of catastrophe. Symptoms associated with chronic anxiety include, but are not limited to, uneasiness, nervousness, nagging uncertainty about future events, headache, fatigue, and subacute autonomic symptoms.

Another embodiment of the invention encompasses a method of treating or preventing a convulsive state in a subject which comprises administering to a subject in need of such treatment or prevention a therapeutically or prophylactically effective amount of a zopiclone maleate salt. A particular method of this embodiment is the treatment or prevention of epilepsy or epileptic seizures. In a further embodiment, the invention provides for reducing the severity and/or frequency of at least one symptom associated with convulsive states which include, but are not limited to, recurrent, sudden, and often brief alterations of consciousness, motor activity, sensory phenomena, and autonomic responses which are often characterized by convulsive seizures and/or tonic or clonic jerking of the extremities. The term "convulsive state" encompasses epilepsy and specific types of epileptic seizures including, but not limited to, Tonic-clonic (Grand Mal), Partial (Focal) seizures, psychomotor (Complex partial) seizures, pyknoepileptic or Absence (Petit Mal) seizure, and Myoclonic seizures.

Another embodiment of the invention encompasses a method of treating or preventing an affective disorder in a subject which comprises administering to a subject in need of such treatment or prevention a therapeutically or prophylactically effective amount of a zopiclone maleate salt. A particular method encompassed by this embodiment is the treatment or prevention of depression. Another method encompassed by this embodiment is the treatment or prevention of attention deficit disorder or attention deficit disorder with hyperactivity. The phrase "treating or preventing an affective disorder" means reducing the severity of at least one symptom associated with a psychological disorder characterized by abnormality of emotional state, including but not limited to, depression, dysthymia, attention deficit disorder, attention deficit disorder with hyperactivity, bipolar disorders, bipolar and manic conditions, and the like. The terms "attention deficit disorder" ("ADD") and "attention deficit disorder with hyperactivity" ("ADDH"), or "attention deficit/hyperactivity disorder" ("ADHD"), are used herein in accordance with the accepted meanings as found in the Diagnostic and Statistical Manual of Mental Disorders, 4th Ed., American Psychiatric Association (1997). In one embodiment, the phrase "treating or preventing depression" means reducing the severity of at least one symptom associated with depression which include, but are not limited to, changes in mood, feelings of intense sadness, despair, mental slowing, loss of concentration, pessimistic worry, agitation, and self-deprecation. Symptoms associated with depression can also be physical symptoms, which include, but are not limited to, insomnia, anorexia, weight loss, decreased energy and libido, weight gain, and abnormal hormonal circadian rhythms.

Another embodiment of the invention encompasses a method of treating or preventing aggressive behavior in a subject which comprises administering to a subject in need of such treatment or prevention a therapeutically or prophylactically effective amount of a zopiclone maleate salt. In certain embodiments, the method includes reducing the frequency and/or severity of at least one manifestation of aggressive behavior which include, but are not limited to, aggressive or socially inappropriate vocal outbursts and acts of physical violence.

Another embodiment of the invention encompasses a method of treating or preventing spasticity or acute muscle spasm spasticity in a subject which comprises administering to a subject in need of such treatment or prevention a therapeutically or prophylactically effective amount of a zopiclone maleate salt. In certain instances the invention provides a method of "treating or preventing spasticity," "treatment and prevention of spasticity," "treating or preventing spasticity and acute muscle spasm," and "treatment and prevention of spasticity and acute muscle spasm," which includes reducing the severity of at least one symptom associated with a range of abnormalities of skeletal muscle regulation that result from problems of the nervous system. A predominant symptom is heightened muscle tone or hyper-excitability of tonic stretch muscle reflexes. Symptoms of acute muscle spasm include, but are not limited to, trauma, inflammation, anxiety, and pain.

Another embodiment of the invention encompasses a method of treating or preventing a behavioral disorder in a subject which comprises administering to a subject in need of such treatment or prevention a therapeutically or prophylactically effective amount of a zopiclone maleate salt. The phrase "treating or preventing a behavioral disorder" means reducing or relieving from at least one symptom of a behavioral disorder, which include, but are not limited to, a subjective sense of terror, a dread of catastrophe, uneasiness, nervousness, uncertainty, headache, fatigue, disturbed thinking, inappropriate effect, auditory hallucinations, and aggressive outbursts.

Another embodiment of the invention encompasses a method of treating or preventing a schizophrenic disorder in a subject which comprises administering to a subject in need of such treatment or prevention a therapeutically or prophylactically effective amount of a zopiclone maleate salt. The phrase "treating or preventing a schizophrenic disorder" means reducing the severity of at least one symptom associated with schizophrenic disorders. Symptoms of schizophrenic disorders include, but are not limited to, psychotic symptoms of disturbed thinking, feeling and general behavior. Specific symptoms of schizophrenic disorders include the inability to form clear, goal-directed thought, and emotional changes such as blunting and inappropriate affect. Other symptoms of schizophrenic disorders include auditory hallucinations, delusions of persecution, threats of violence, minor aggressive outbursts, aggressive behavior, disturbances of movement such as significant overactivity and excitement, and retardation and stupor.

Another embodiment of the invention encompasses a method of treating alcohol or drug addiction in a subject which comprises administering to a subject in need of such treatment a therapeutically or prophylactically effective amount of a zopiclone maleate salt. As used herein, the phrase "treating alcohol or drug addiction" means reducing at least one symptom of disease or conditions related to alcohol or drug addiction including, but not limited to, drug or alcohol addiction or symptoms of withdrawal from alcohol or drugs. Symptoms of withdrawal include, but are not limited to, depression, pain, fever, restlessness, lacrimation, rhinorrhea, uncontrollable yawning, perspiration, piloerection, restless sleep, mydriasis, twitching and muscle spasms, severe aches in the back, abdomen and legs, abdominal and muscle cramps, hot and cold flashes, insomnia, nausea, vomiting, diarrhea, coryza and severe sneezing, and increases in body temperature, blood pressure, respiratory rate, and heart rate. Another embodiment of the invention encompasses a method of treating or preventing drug withdrawal, alcohol withdrawal, symptoms of drug withdrawal, or symptoms of alcohol withdrawal in a subject which comprises administering to a subject in need of such treatment a therapeutically or prophylactically effective amount of a zopiclone maleate salt.

In another aspect, the invention provides a use of the maleate salt of the invention in the manufacture of a medicament for treating or preventing any one of the disorders disclosed herein in a patient.

In one embodiment, the invention provides a use of the maleate salt of the invention in the manufacture of a medicament for treating or preventing sleep disorder in a patient.

In one embodiment, the invention provides a use of the maleate salt of the invention in the manufacture of a medicament for treating or preventing anxiety in a patient.

In certain aspects, the racemic zopiclone can be utilized herein in the same manner as described for the S-isomer eszopiclone. However, it is recognized that use of eszopiclone can provide advantages over use of the racemic zopiclone and thereafter use of eszopiclone will be preferred for many applications.

In a specific method, the zopiclone maleate salt used in the treatment of the above disorders is stereomerically pure.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

An effective amount" refers to an amount of a compound, which confers a therapeutic effect on the treated subject. The therapeutic effect can be objective (i.e., measurable by some test or marker) or subjective (i.e., subject gives an indication of or feels an effect). Effective doses will also vary depending on route of administration.

As used herein, and unless otherwise specified, the terms "prevent," "preventing," "prevention," and "prophylactic" refer to the prevention of the onset, recurrence or intensification of a disorder disclosed herein. The terms "prevent," "preventing," "prevention," and "prophylactic" include ameliorating and/or reducing the occurrence of symptoms of a disorder disclosed herein.

Physical Properties of Salt

The maleate salt described above has exhibited improved taste characteristics relative to the free base compound, as demonstrated in the examples which follow. Taste assessments were made with "Electronic-tongue" (E-tongue) analysis systems and also in human taste trials. Preferred salt compounds have at least a one unit difference on an E-tongue analysis relative to eszopiclone, more preferably at least a 2 or 3 unit difference on an E-tongue analysis relative to Eszopiclone. E-tongue analysis is suitably performed as described in Example 3 which follows using E-tongue apparatus commercially available from Alpha-mos (Hillsborough, N.J.). As referred to herein, a specified unit difference on an E-tongue analysis refers to a value using a protocol as specified in Example 3 which follows.

The results in the E-tongue analysis are bolstered by the finding that the maleate salt exhibits less bitterness than the free base when tested with human subjects as described in Example 5 below.

It also has been found that the present salt compounds exhibit good solubility and dissolution characteristics, as shown in Example 4 which follows.

Pharmaceutical Compositions

The present invention relates to pharmaceutical compositions containing the maleate salt of the dextrorotatory isomer of zopiclone, the levorotatory isomer of zopiclone, or its racemic mixture, in the pure state or in the presence of a diluent or a coating. These compositions can be employed orally, rectally or parenterally.

Pharmaceutical compositions and dosage forms of the invention comprise one or more of the active ingredients disclosed herein. Pharmaceutical compositions and dosage forms of the invention typically also comprise one or more pharmaceutically acceptable excipients or diluents.

The term "pharmaceutically acceptable," as used herein, refers to a component that is, within the scope of sound medical judgment, suitable for use in contact with the tissues of humans and other mammals without undue toxicity, irritation, allergic response and the like, and is commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

The invention also provides compositions comprising an effective amount of the maleate salt of zopiclone and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disorder can contain larger amounts of one or more of the active ingredients it comprises than a dosage form used in the chronic treatment of the same disease. Similarly, a parenteral dosage form can contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets can contain excipients not suited for use in parenteral dosage forms. The suitability of a particular excipient can also depend on the specific active ingredients in the dosage form. For example, the decomposition of some active ingredients can be accelerated by some excipients such as lactose, or when exposed to water. This invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art. In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and can be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components can be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

The maleate salt of zopiclone can, for example, be administered with a dosage ranging from about 0.001 to about 0.2 mg/kg of body weight, alternatively dosages between 0.1 mg and 15 mg/dose, or between about 0.1 mg and about 10 mg/dose, or preferably between about 0.2 mg and about 5 mg/dose, or according to the requirements of the particular therapy. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that can be combined with the carrier materials to produce a single dosage form will vary depending upon the host treated and the particular mode of administration. In some embodiments, such preparations contain from about 20% to about 80% (w/w) active compound. In some embodiments, such preparations contain from about 0.5% to about 20% active compound. A typical preparation will contain from about 0.5% to about 5% active compound (w/w).

Lower or higher doses than those recited above can be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Like the amounts and types of excipients, the amounts and specific types of active ingredients in a dosage form can differ depending on factors such as, but not limited to, the route by which it is to be administered to patients. In human therapy, the doses depend on the effect sought and the treatment period; taken orally, they are generally between 0.5 and 15 mg per day for an adult. For many applications, unit dosages containing 0.5 mg, 1 mg, 2 mg or 3 mg of a present eszopiclone salt will be suitable. In some embodiments, the unit dosages of the eszopiclone salts can be adjusted to contain the molar equivalent of 0.5 mg, 1 mg, 2 mg or 3 mg of eszopiclone freebase.

The following non-limiting examples are illustrative of the invention.

EXAMPLE 1

Synthesis of (S)-Zopiclone Maleate

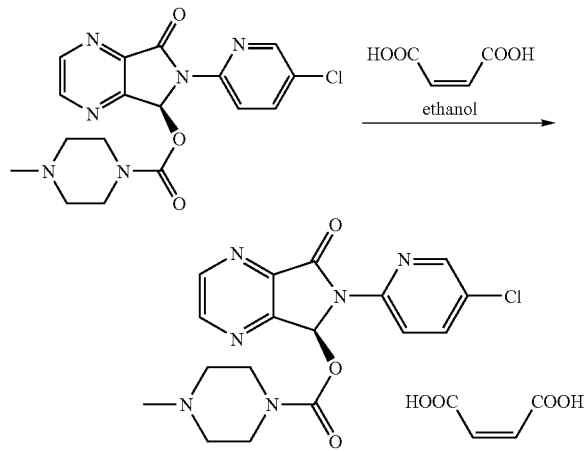

A reactor was charged with 0.101 g (S)-zopiclone and 0.040 g maleic acid. The mixture was charged with 18 g ethanol, and agitated. The slurry was heated to 60° C. and aged for 90 minutes. The slurry was cooled to 20° C. and aged for 60 minutes. The reaction was filtered, washed once with 0.5 g ethanol, dried in vacuo at approximately 50° C. for approximately 6 hr, and provided the titled compound in 76% yield.

EXAMPLE 2

Alternate Synthesis of (S)-Zopiclone Maleate

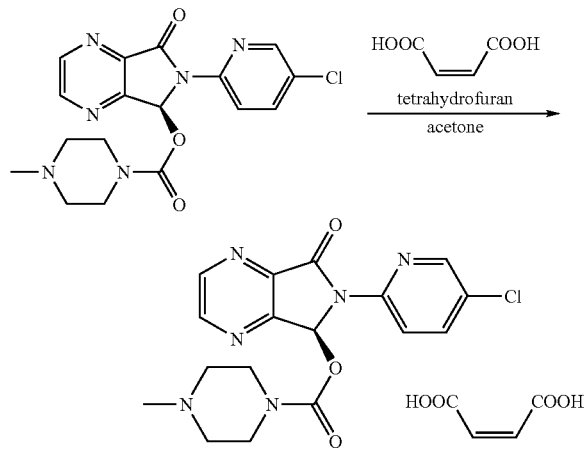

A reactor was charged with 10.1 g (S)-zopiclone, the reactor was charged with 512.6 g of tetrahydrofuran, and agitation was started. The mixture was heated to 50° C. To the reactor was added a 10% of a solution created by combining 3.20 g of maleic acid with 155.7 g acetone. The mixture was seeded with 250 mg (S)-zopiclone maleate and aged for 25 minutes. The remaining acid solution was added over 25 minutes. (total acid eq=1.05). The mixture was aged for 30 minutes, cooled to 20° C. at 0.5° C./minute, aged for 2 hours, filtered and washed once with 70 g tetrahydrofuran, and dried in vacuo until no further weight loss at 45° C. (~4 h) to provide the titled compound in 94% yield.

EXAMPLE 3

Bitterness Results Using E-Tongue

The α Astree II Bitterness Prediction Module (BPM) and Electronic Tongue (E-Tongue) was utilized to perform taste assessments. The sensory (E-tongue) apparatus utilized is commercially available (Alpha-mos, Hillsborough, N.J.) and includes three arrays of seven sensors with the third array utilized to assess bitterness of chemical identities. The bitterness results were obtained with the α Astree II BPM used in a pharmaceutical configuration for bitterness assessment of Eszopiclone, and its maleate salt form prepared at various concentrations using the third sensor array.

When analyzing a sample on the α Astree II Electronic Tongue, basic parameters/experimental conditions, such as analysis time and stirring rate per sample were established in accordance with standard operation of the analysis system. The various methods were saved on the BPM for the analysis of each test sample. Each method utilized all seven sensors (BD, EB, JA, JG, KA, OA, and OB) on sensor array 3 to perform an instrumental characterization of the prepared formulations.

Solutions of caffeine (0.05 and 0.5 mg/mL), acetaminophen (0.5 and 3.0 mg/mL), quinine (0.04 and 0.01 mg/mL), and prednisolone (0.25 and 0.5 mg/mL), were prepared to create a calibration curve, partial least square (PLS) to correlate the sensory panel scores and the measurements/values obtained from the prepared solutions of Eszopiclone and its maleate salt forms from the BPM.

Eszopiclone and its maleate salt were prepared as solution in deionized water at freebase equivalent concentrations of 0.002 mg/mL and 0.02 mg/mL for analysis.

BPM data analysis model is based on a Partial Least Square PLS statistical data treatment. The PLS model allowed for correlation of the instrument result (sensor responses) to a BU (Bitterness Unit) defined by the sensory panel. The proposed scale of BU is from 1 to 20, which respectively corresponds to a non detectable bitterness and an unacceptable bitterness.

The in vivo measurements were then performed on a 1-20 scale where the bitterness intensity increases for higher marks. This scale was divided into 5 different categories: non detectable bitterness from marks 1 to 4.5; slight bitter taste from marks 4.5 to 8.5; acceptable bitterness from marks 8.5 to 12.5; limit but acceptable bitterness from marks 12.5 to 16.5; and non acceptable bitterness from marks 16.5 to 20. The results of the e-tongue data are provided in Table 1. Table 1 shows that the maleate salt has a predicted bitterness of 8 at 0.02 mg/mL, and a predicted bitterness of 6.5 at 0.002 mg/mL. Desirable compositions have at least a one unit difference on an E-tongue analysis relative to control (in this case the corresponding free base).

TABLE 1

| Average Predicted Bitterness | | |
|---|---|---|
| Sample | Concentration | Average Predicted Bitterness |
| Free base | 0.02 mg/ml | 15.6 |
|  | 0.002 mg/ml | 8.4 |

TABLE 1-continued

Average Predicted Bitterness

| Sample | Concentration | Average Predicted Bitterness |
|---|---|---|
| Maleate | 0.02 mg/ml | 8 |
| | 0.002 mg/ml | 6.5 |

EXAMPLE 4

Solubility and Dissolution

The aqueous solubility was determined by taking a filtered aliquot of an equilibrated (24 hour at ambient) suspension of the salt in water. The aliquot was diluted and analyzed by HPLC (Waters). The data was compared to a standard curve generated from a set of solutions of known concentrations. The standard curve and the samples were analyzed using a HPLC using the following conditions:
Column: Symmetry C-18, 5 um, 15 cm×3.9 mm (Waters)
Mobile Phase: 0.05 M $KH_2PO_4$—0.01 M Hexanesulfonic Acid/THF (1000:125) (Apparent pH 5.0)
Column Temp: 20-30° C.
Flow Rate: 1.0 mL/min
Wavelength: 305 nm
Run Time: 15 min (zopiclone retention time is 9.5-10 min)

TABLE 2

Water Solubility Data for Eszopiclone Salts

| Compound | Solubility(mgA/mL) | $pH^2$ |
|---|---|---|
| Freebase | $0.2^1$ | 7.6 |
| Maleate | 9 | 4.4 |

[1] 24-hour value; experiment stopped because significant degradation was observed
[2] pH measured at saturation

TABLE 3

Intrinsic Dissolution Data for Eszopiclone Salts in Isotonic 50 mM Acetate (pH 4.5) Buffer at 37° C.

| Compound | Run 1 ($mgA/cm^2/min$) | Run 2 ($mgA/cm^2/min$) | Average ($mgA/cm^2/min$) |
|---|---|---|---|
| Freebase | 0.6 | 0.5 | 0.5 |
| Maleate | 1.4 | 1.2 | 1.3 |

The intrinsic dissolution (Table 3) was determined using USP 28 method <1087> (*United States Pharmacopeia, The National Formulary*, USP 28, 28th edition, Rockville, Mass., 2005). Preparation of each test sample was performed as per USP 28 method <1087> by weighing and transferring the material to the die cavity and compressing for 1 minute at the minimum compression pressure necessary to form a nondisintegrating compacted pellet. The dissolution media used was isotonic 50 mM acetate buffer (pH 4.5) at 37° C. and speed was set at 50 rpm. Each run was halted at 5 min, irrespective of the percent dissolved. Each salt was run in duplicate.

Dissolution over time of eszopiclone maleate salt was compared to that of free base at room temperature (FIG. 1) in pH 4.5 20 mM acetate buffer using Hanson Research SR8-Plus Dissolution Apparatus and C-Technologies Fiber Optic Probes. A standard dissolution protocol was used. For example, 100.12 mg Eszopiclone free base (MW 388.81) or 129.98 mg eszopiclone maleate salt (MW 504.88; purity 99.9%) was added to an empty vessel. 500 ml of pH 4.5 20 mM acetate buffer was added to each of the vessels and mixed at 50 rpm paddle speed. The dissolution program was started immediately and readings were taken at 350 nm for 60 min (every 1 min for 10 min and then every 10 min). Each sample was run in triplicate.

EXAMPLE 5

Bitterness Results in an Open-label Taste Assessment in Healthy Human Subjects

The Flavor Profile is a descriptive sensory analysis method used to measure the type and intensity of attributes in products and ingredients. It is based on the concept that flavor consists of identifiable taste, odor (aroma), and chemical feeling attributes, plus an underlying complex of attributes not separately identifiable. The method consists of formal procedures for describing and assessing the flavor of a product in a reproducible manner.

Seven-point scales are used to measure the intensity or strength of the flavor character notes as well as the amplitude, as shown below:

| Value | Intensity | Amplitude |
|---|---|---|
| 0 | None | None |
| ½ | Very Slight | Very Low |
| 1 | Slight | Low |
| 1½ | Slight-to-Moderate | Low-to-Moderate |
| 2 | Moderate | Moderate |
| 2½ | Moderate-to-Strong | Moderate-to-Strong |
| 3 | Strong | Strong |

Intensity is a constant scale; that is, when sweetness is designated at a slight-to-moderate strength (1½) in both chocolate and orange juice, for example, the sweetness level detected can be related to reference materials of a slight-to-moderate level of sweetness exemplified by a certain concentration of sugar (sucrose). A description of aftertaste, the sensations that are still present in the mouth after swallowing, is also included in the Flavor Profile. Aftertaste was measured in terms of intensity ratings at various time intervals.

For the purpose of testing the compounds of the invention, the flavor profile panel consisted of four persons who have normal ability to smell and taste, have been trained in fundamental sensory principles and all aspects of the Flavor Profile technique and have considerable experience as panel members. The samples to be profiled were uniform and representative. Sample preparation and presentation were standardized and controlled. Each panel member received an aliquot for his/her own independent analysis.

Eszopiclone maleate was evaluated as a solution in water. Each panelist constituted his/her individual sample and mixed the solution with a magnetic stirrer for 20 minutes. The samples were prepared at 0.01 mg/5 mL, 1.0 mg/5 mL and 3.0 mg/5 mL. The 0.01 mg/5 mL concentration is believed to approximate a concentration that could be encountered during the brief period that a 3 mg tablet resides in the typical patient's mouth. For that reason, the results at 0.01 mg/5 mL are considered most clinically relevant. The 1.0 mg/5 mL concentration is probably the upper limit for exposure and would be considered quite uncommon. Achieving a 3.0 mg/5 mL concentration under normal conditions of oral administration would require chewing the whole tablet, which is considered not relevant for the present purposes. The panelists sipped the full 5 mL solution, swished it around the oral cavity and expectorated after 10 seconds. During this time the panelists independently evaluated and recorded the initial flavor characteristics. The panelists then independently evaluated and recorded the aftertaste characteristics at 1, 3, 5, 10, 15, 20, 25 and 30 minutes. The taste element that is most noticed by patients taking eszopiclone free base is bitterness. The results of the test for bitterness are shown in the following table:

TABLE 4

Human Taste Bitterness Results for Eszopiclone Maleate Salt

| dose | t = 0 | t = 1 | t = 3 | t = 5 | t = 10 | t = 15 | t = 20 | t = 25 | t = 30 |
|---|---|---|---|---|---|---|---|---|---|
| 0.01 mg/5mL free base | 1.6 | 1.7 | 1.7 | 1.5 | 1.3 | 1.1 | 0.9 | 0.6 | 0.4 |
| 0.01 mg/5mL salt | 0.9 | 1.2 | 1.1 | 0.9 | 0.6 | 0.4 | 0.4 | 0.3 | 0 |
| 1.0 mg/5mL free base | 2.7 | 2.8 | 2.6 | 2.4 | 2.2 | 2.0 | 1.8 | 1.5 | 1.4 |
| 1.0 mg/5mL salt | 2.7 | 2.4 | 2.1 | 2.0 | 1.8 | 1.7 | 1.6 | 1.4 | 1.2 |

Although the salt was tested at 3.0 mg/5 mL, the free base was not, so comparative data are not available.

EXAMPLE 6

Exemplary Compositions

Suitable ingredients of a tablet dosage form using eszopiclone maleate as the active ingredient are provided in Table 5. Tablets containing 3 mg of active product and having the following composition can be prepared according to a usual technique:

TABLE 5

| Exemplary Composition | |
|---|---|
| Maleate Salt | 0.003 g* |
| Microcrystalline Cellulose | 0.060 g |
| Calcium Phosphate | 0.035 g |
| Magnesium Stearate | 0.005 g |

*Adjust to contain molar equivalent of 0.003 g of freebase eszopiclone

Tablets of other strengths can be prepared by altering the ratio of active ingredient to pharmaceutically acceptable carrier, the compression weight, or by using different punches.

Incorporation by Reference

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications. In case of conflict, the present application, including any definitions herein, will control.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An oral pharmaceutical dosage form comprising a maleate salt of eszopiclone and a pharmaceutically acceptable carrier.

2. An oral pharmaceutical dosage form according to claim 1 wherein said maleate salt of eszopiclone is of formula

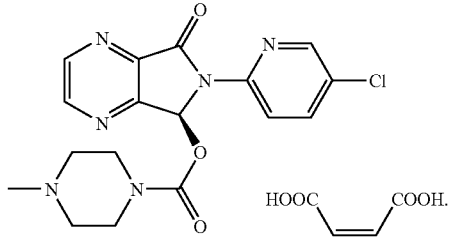

* * * * *